United States Patent [19]

Hidaka et al.

[11] Patent Number: 4,959,796

[45] Date of Patent: Sep. 25, 1990

[54] METHOD OF PRODUCING ANALYTICAL CURVE

[75] Inventors: Seiji Hidaka; Takashi Ishihara, both of Tachikawa; Takehiko Hamaguchi, Hachioji; Nobuaki Sugiyama, Hino; Kosuke Toura, Hachioji, all of Japan

[73] Assignee: Konica Corporation, Tokyo, Japan

[21] Appl. No.: 268,928

[22] Filed: Nov. 9, 1988

[30] Foreign Application Priority Data

Nov. 10, 1987 [JP] Japan .................................. 62-283763

[51] Int. Cl.$^5$ .............................................. G06F 15/42
[52] U.S. Cl. ...................................... 364/497; 356/39; 364/496; 364/474.01
[58] Field of Search ............... 356/243, 338, 339, 246, 356/39, 325, 445, 45; 422/64, 67; 364/496, 498, 497, 571.01, 571.02, 571.04, 579, 553, 413.08, 413.09; 250/252.1 R, 252.1 A

[56] References Cited

U.S. PATENT DOCUMENTS

| | | | |
|---|---|---|---|
| 3,828,173 | 8/1974 | Knepler | 364/498 |
| 4,202,033 | 5/1980 | Strobel | 364/413.08 |
| 4,373,818 | 2/1983 | Yamamoto et al. | 356/445 |
| 4,627,014 | 12/1986 | Lo et al. | 356/39 |
| 4,706,207 | 11/1987 | Hennessy et al. | 356/39 |
| 4,744,657 | 5/1988 | Aralis et al. | 374/498 |
| 4,832,488 | 5/1989 | Hirai et al. | 356/243 |

FOREIGN PATENT DOCUMENTS 62-32344  2/1987  Japan.
63-111446 5/1988  Japan.

Primary Examiner—Kevin J. Teska
Attorney, Agent, or Firm—Finnegan, Henderson, Farabow, Garrett, and Dunner

[57] ABSTRACT

A method of producing an analytical curve for an analyzing apparatus which provides an analysis result on the basis of the analytical curve in response to a measurement value obtained by photoelectrically measuring light intensity reflected from a slide to be analyzed. A plurality of reference slides are measured by first analyzing apparatus which has a predetermined analytical curve, thereby obtaining a plurality of first measurement values and providing a plurality of first analysis results. The plurality of reference slides are further measured by second analyzing apparatus, thereby obtaining a plurality of second measurement values. Analytical curve for the second analyzing apparatus for produced on the basis of a relation between the first measurement values and the second measurement values so that a plurality of second analysis results correspond to the plurality of first analysis results.

13 Claims, 9 Drawing Sheets

METHOD OF PRODUCING ANALYTICAL CURVE

BACKGROUND OF THE INVENTION

The present invention relates to a method of generating conversion formulas for obtaining analysis values and more particularly, to a method wherein such formulas enables the analysis value obtainable by, for example, an analyzer manufactured to be delivered to a customer, to coincide with those obtained by a reference analyzer.

There is a conventional analyzer in which a specimen such as blood and serum is dripped onto a slide to be analyzed that comprises a transparent support provided thereon at least one reagent layer and that exhibits change in optical density once a specimen adheres thereto, thereby reflected density is measured in order to determine presence/absence of a specific component or amount of the component. In such an analyzer, a slide to be analyzed is irradiated with light, and reflected light is collected, thereby based on the reflected light, progress, results or the like of specimen-reagent reaction is determined, and the measurement value is arithmetically processed to determine an analysis value.

However, the degree of reaction on a slide to be analyzed is not linear relative to the optical density of the reflected light. Therefore, if a measurement value is based on an optical reflection density, some conversion formula is indispensable for converting the optical density into the analysis value of concentration of a specific component in a specimen or of enzyme concentration.

With respect to such a conversion formula, it is noted in "Spectrometry in Clinical Biochemical Tests" (by Yoshino and Ohsawa, Gakkai Shuppan Center) that the correlation between a reflectance and concentration of substance can be defined by Kubelka—Munk's formula. This literature further mentions application of Williams—Clapper's formulas and those based on Beer's law. A technique using a conversion formula is disclosed in Japanese Patent Publication Open to Public Inspection (hereinafter referred to as Japanese Patent O.P.I. Publication) No. 32344/1987, while the same applicant proposes introduction of conversion formulas represented by hyperbolas, in Japanese Patent Open to Publication No. 111446/1988.

SUMMARY OF THE INVENTION

Such a conversion formula should be necessarily incorporated into another analyzer other than a reference analyzer. In doing so, one possible measure is as follows: the reference analyzer that has a built-in conversion formula is first prepared, and then, an analysis value obtained by another analyzer is adjusted to that of the reference analyzer, thereby measuring accuracy is improved. According to this arrangement, when incorporating an appropriate conversion formula into another analyzer by dripping a specimen onto an actual slide that is measured by a reference analyzer as well as by the other analyzer, where the analysis value of the other analyzer is adjusted to that of the reference analyzer, there occurs a problem due to fluctuation in analysis values based on dripped specimen. Dripping a specimen incurs more problems; for example, this technique involves a reaction time, and, accordingly, time for determining an analysis value becomes disadvantageously long.

With the above-mentioned problems taken into account, the present invention has for its object to provide a method of readily generating a conversion formula for obtaining an analysis value based on a measured value, at a lower cost, and in a shorter duration.

There is provided, to achieve the above-mentioned object, a method for generating a conversion formula wherein, on the basis of the measured values which are obtained by measuring a plurality of reference slides by a reference analyzer as well as by another analyzer, the conversion formula corresponds the analysis value of the other analyzer to the analysis value of the reference analyzer.

In the method embodying the present invention, a plurality of reference slides, which are prepared preliminarily and do not require dropping of a specimen thereon, are subjected to the measurement by both a reference analyzer and another analyzer so as to obtain measured values; the other analyzer is incorporates a conversion formula which makes its analysis values correspond to those of the reference analyzer on the basis of the measured values by the two analyzers.

BRIEF DESCRIPTION OF THE DRAWINGS

The drawings appended illustrate preferred embodiments of the present invention, wherein.

DETAILED DESCRIPTION OF THE INVENTION

The preferred embodiments of the present invention will be described hereunder with reference to the drawings appended.

Figure 1:
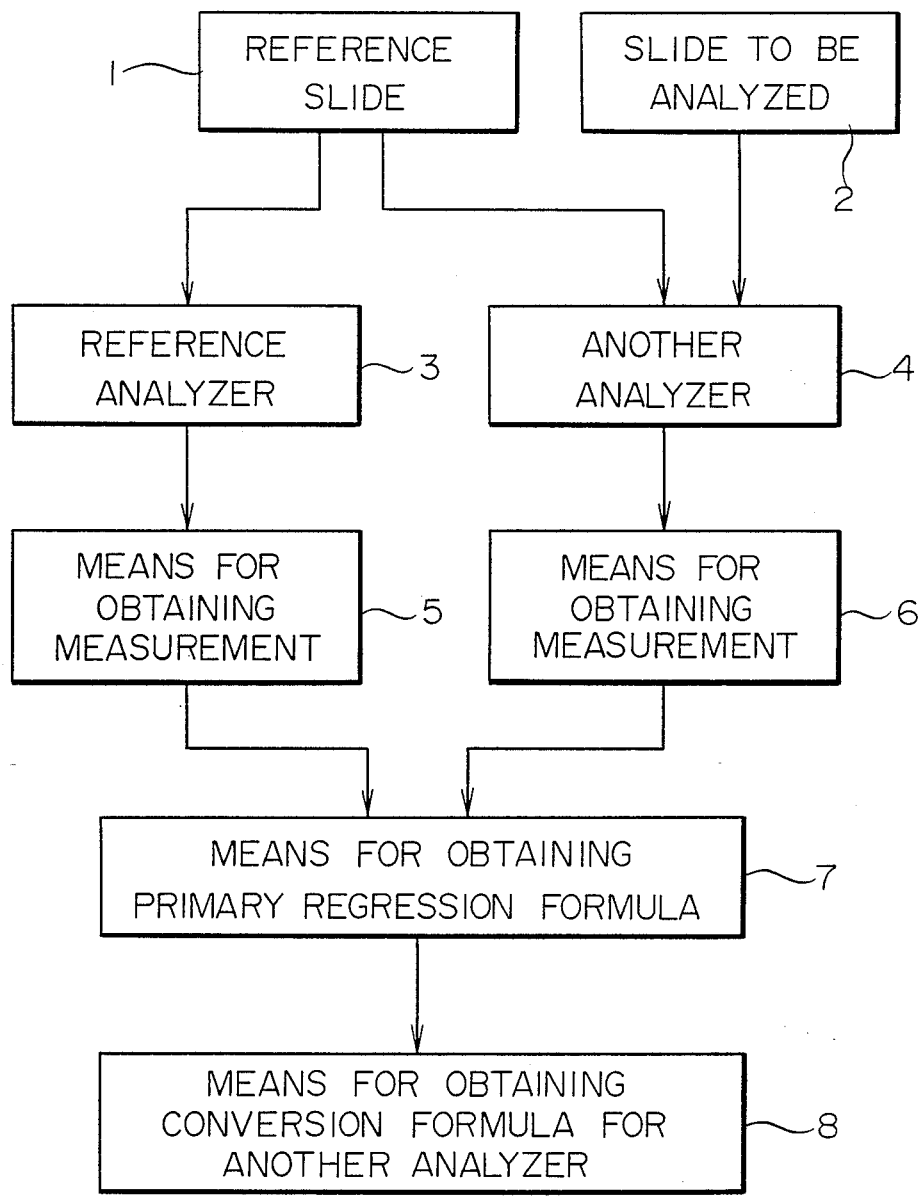
FIG. 1 is a block diagram explaining the invention as to its basic constitution.

FIG. 1 shows a first preferred embodiment of the present invention in a block diagram explaining its basic constitution.

Numeral 1 in this diagram indicates a reference slide, which is made of color paper, plastic, ceramic or the like, and has a shape identical to that of a slide 2 to be analyzed. In this embodiment, a plurality of reference slides 1 are prepared, and each of reference slides 1 is dyed in a predetermined color and is designed to give a specified reflection density when subjected to the measurement. The plurality of reference slides 1 are measured by both a reference analyzer 3 and another analyzer 4.

Measurements (reflection density) are obtained by means for obtaining measurement 5, 6 provided respectively on the analyzers 3, 4. A plurality of measurements obtained from the plurality of reference slides 1 by each analyzer are entered into means for obtaining primary regression formula 7 so as to obtain a primary regression formula that represents a relation between the measurements.

The so-obtained primary regression formula is substituted into the measurement term in the conversion formula in the reference analyzer 3 by "means for obtaining conversion formula for another analyzer" 8 so as to obtain a conversion formula whereby the analysis value obtained by the other analyzer 4 is made to agree with that of the reference analyzer 3. This conversion formula for obtaining an analysis value (concentration of a substance or enzyme activity value of a component of a specimen) from a measurement is incorporated into the other analyzer 4 so that an analytical curve corresponding to an item of measurement of a slide to be analyzed 2 can be determined.

One useful conversion formula possibly incorporated into the reference analyzer 3 is as follows:

$$Y = \frac{B}{X - A} + C \quad (1)$$

which is described in Japanese Patent Open to Publication No. 111446/1988.

In the conversion formula (1), Y represents an analysis value which is the concentration of a substance as a component of a specimen, or the enzyme activity value; X represents a measurement which, in the case of end point measuring technique, is determined based on the reflection density, and, in the case of rate measuring technique, is determined based on change in reflection density that occurs as time elapses; A, B and C are constants determined based on the type of a slide to be analyzed and on characteristic values of the analyzer.

Accordingly, if the primary regression formula obtained by the means for obtaining primary regression formula is, for example:

$$X = ax' + b \quad (2)$$

wherein X represents a measurement obtained by reference analyzer 3 and X' represents a measurement obtained by another analyzer 4. When the primary regression formula (2) is substituted into the measurement term of the aforementioned conversion formula (1), there can be obtained and loaded onto the other analyzer 4 a conversion formula expressed as $$Y = \frac{B}{(aX' + b) - A} + C = \frac{B/a}{X' - (A - b)/a} + C \quad (3)$$

Therefore, when a slide to be analyzed 2 is subjected to measurement by this analyzer 4 the conversion formula (3) enables the analyzer to produce from the reflection density measured an analysis value which agrees with that obtainable by the reference analyzer 3.

This conversion formula is generated by a computer provided outside the analyzer. It is also possible to obtain the formula by analyzer alone, by loading numerical data, which are processed by processing raw data, into the analyzer.

Figure 2:
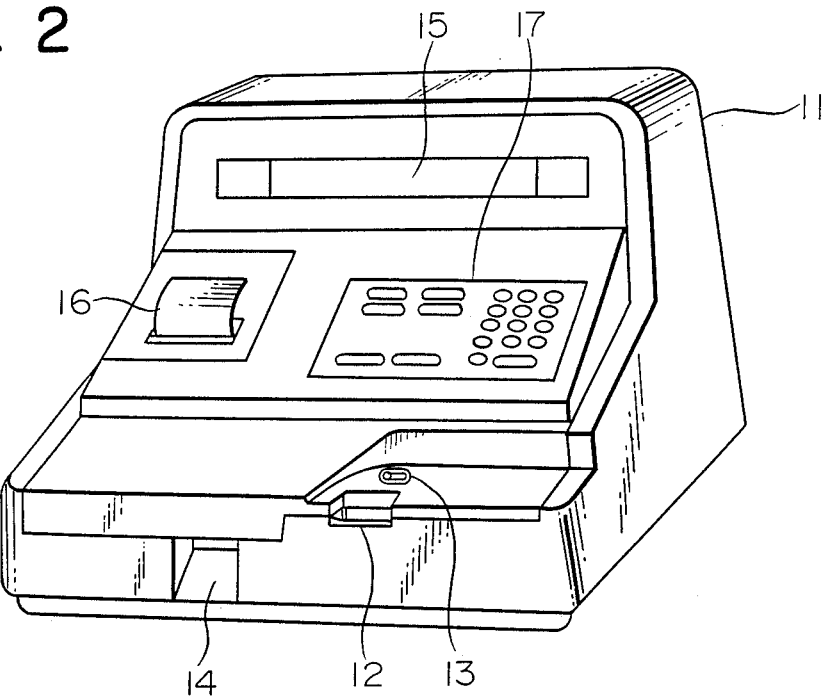
FIG. 2 is an analyzer represented in a schematic elevational view in perspective.

FIG. 2 shows a front elevational view of an analyzer embodying the present invention. In the analyzer body 11, there are provided a slide insertion part 12, specimen dripping part 13, slide discharge part 14, display 15, printer 16 and operation/control section 17. The display 15 indicates a description of an operation, error messages and the like.

Figure 3:
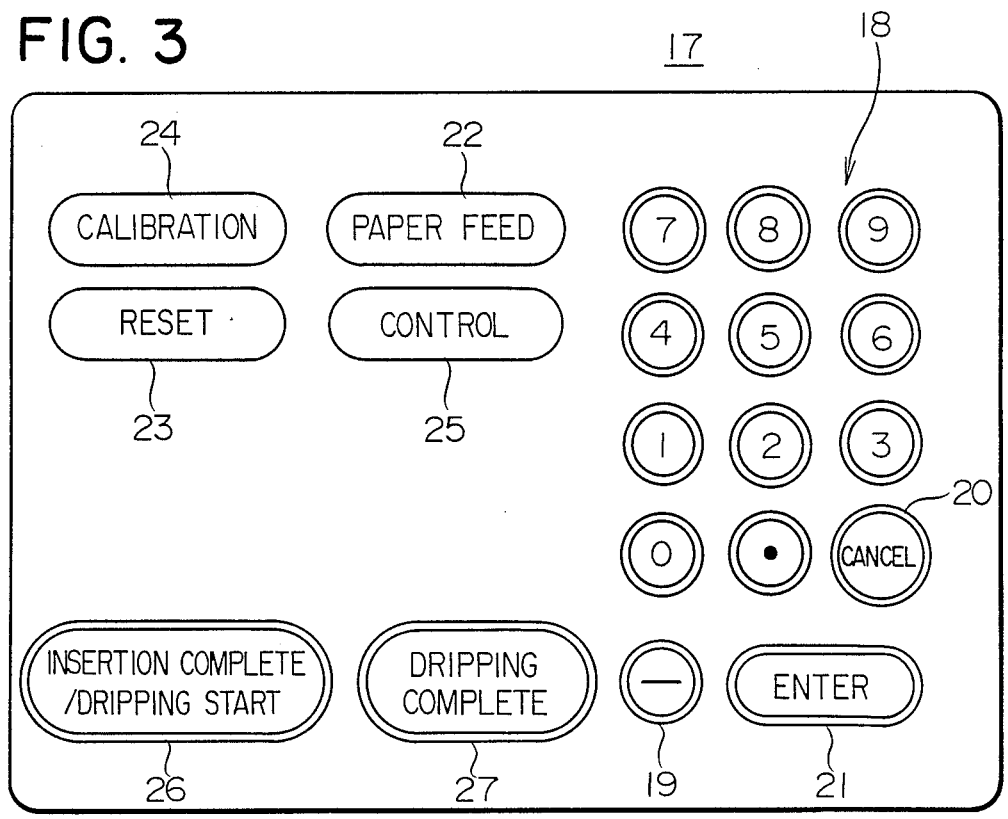
FIG. 3 illustrates the operation control panel of the analyzer in FIG. 2.

FIG. 3 shows the operation/control section 17 provided with a set of numerical keys 18 for entering the date, etc.; minus key 19 for entering negative values; cancel key 20 for cancelling wrong entries such as in numerals; enter key 21 for entering numerals; paper feed key 22 for feeding recording sheet; reset key 23 used when a wrong slide has been loaded or the dripping of specimen is stopped; calibration key 24 for correcting the regression with the measurement by another analyzer or for calibrating a slide to be analyzed; control key 25 for making conversion formulas, decreasing warm-up time, for changing the indication on the display during the dripping, accessing stored data, changing the unit of measurement, changing the date, and the like; insertion complete/dripping start key 26 used once a slide to be analyzed has been loaded, and this key is also used to start dripping a specimen; and dripping complete key 27 used when the dripping has been completed.

Figure 4:
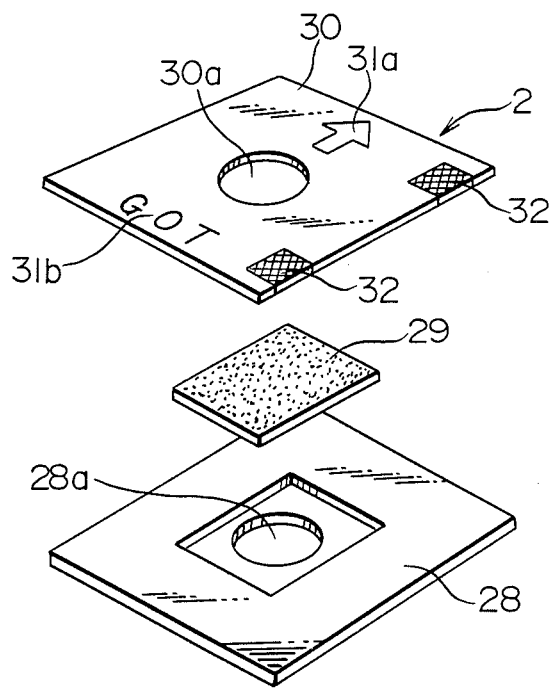
FIG. 4 is an exploded view of a slide to be analyzed in perspective.
Figure 5:
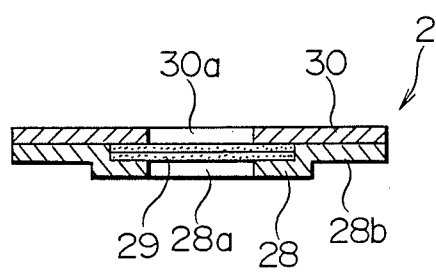
FIG. 5 represents a cross section of a slide to be analyzed.

FIG. 4 illustrates, in an exploded perspective view, and FIG. 5, in a cross-sectional view, "a slide to be analyzed" 2. The slide to be analyzed 2 comprises a mount base 28 having in its central recess a through hole 28a for photometry, wherein into the recess is loaded an analyzing element 29 having a reagent; a mount cover 30 centrally having a through hole 30a for specimen dripping is fitted to the mount base 28, and covers the analyzing element 29, wherein the mount base 28 and the mount cover 30 are bonded together with bonding means such as ultrasonic bonding. The mount base 28 is stepped at two sides 28b as a guide for insertion in place and the mount cover 30 has on the surface indications which are an arrow 31a showing the direction of loading a slide, measurement item description 31b, and a measurement item ID code 32 for recognition of the measurement item.

There are differences among the "slides to be analyzed" 2 with respect to the method and time of the photometric measurement as well as the measurement item. The slides suitable for end-point measurement are set for photometric measurement after an interval of 7 minutes following the completion of the dripping, examples of such slides being those of glucose (Glu), total cholesterol (T-Cho), hemoglobin (Hb), urea nitrogen (BUN), urea acid (UA), total protein (TP), albumin (Alb), triglyceride (TG), and total bilirubin (T-Bil). The slides 2 which are suitable for rate measurement are divided into two groups; the first group, such as glutamic-oxaloacetic transaminase (GOT) and glutamin-pyruvic transaminase (GPT), is set for the first photometric measurement after an interval of 7 minutes and the second measurement 11 minutes after the dripping and the second group, such as alkaline phosphatase (ALP) and lactate dehydrogenase (LDH), is set for the first photometric measurement after an interval of 3.5 minutes and for the second measurement both 7 minutes after the dripping.

The reasons for the first photometric measurement in the rate measurement technique, i.e. 3.5 minutes after specimen dripping are that this allows longest possible duration for specimen dripping, and that this time setting, 3.5 minutes, can attain required measurement accuracy. The reason why, for some slides, the first measurement is performed 7 minutes after specimen dripping as in the case of the end point measurement technique is that, as known from experimental results and as described in Japanese Patent Application No. 75997/1986, there is little, if any, adverse effect by interfering substances, hence higher accuracy.

Figure 6:
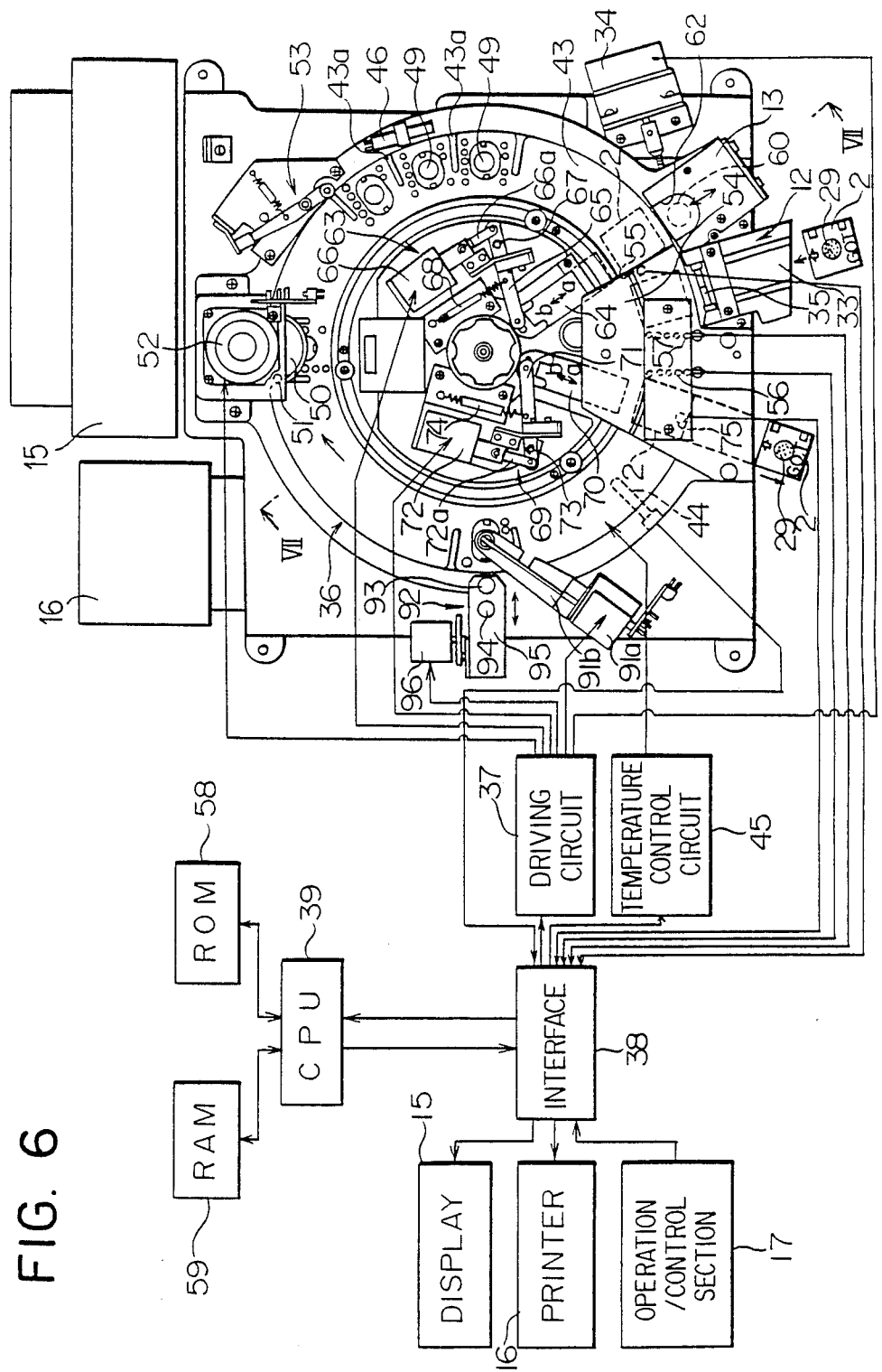
FIG. 6 illustrates the mechanism of an analyzer in a schematic as well as block diagram.

FIG. 6 schematically illustrates the mechanism and configuration of an analyzer embodying the present invention.

Once a slide to be analyzed 2 is inserted through a slide insertion part 12 with the stepped side 28b fitted on an insertion frame 33 so as to be carried into an incubation unit 36 by a slide roller 35 driven by an insertion motor 34. A CPU 39 controls the insertion motor 34 via a driving circuit 37 and via an interface 38 so that the motor is actuated only when the slide 2 can be inserted, thereby insertion of slides 2 is restricted to a number within the processing capacity.

Figure 7:
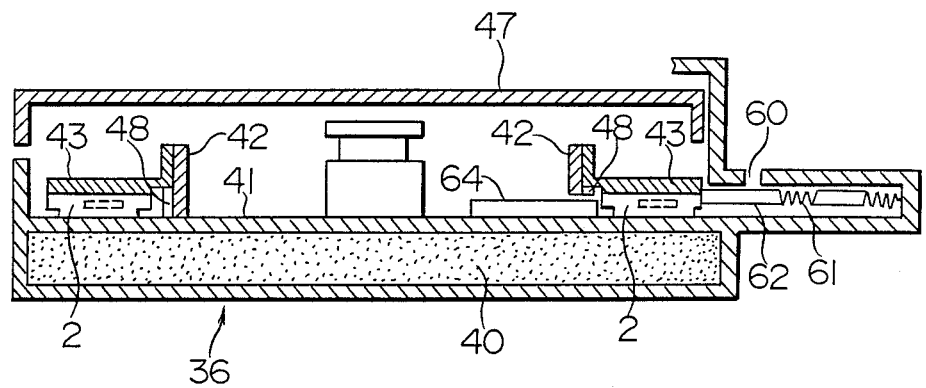
FIG. 7 is a cross section taken along line VII—VII in FIG. 6.

The incubation unit 36 comprises, as shown in FIG. 7, a constant temperature heater plate 41 whose temperature is kept constant by heat radiating liquid 40 it houses; and a disk 43 which is transporting means axially supported on a rim 42 placed on the constant temperature heater plate 41. The heat radiating liquid 40 is provided with a temperature sensor 44, wherein the liquid temperature is regulated using an unshown heater that is controllingly actuated by the CPU 39 via a temperature control circuit 45 based on temperature data from the temperature sensor 44. A thermostat 46 is also provided as means for secure control of the temperature in order to prevent overheating. The disk 43 moves the slides to be analyzed 2 in a circumferential circle. This disk 43 has a heat-insulating cover 47 over it with a certain space therebetween.

Figure 8:
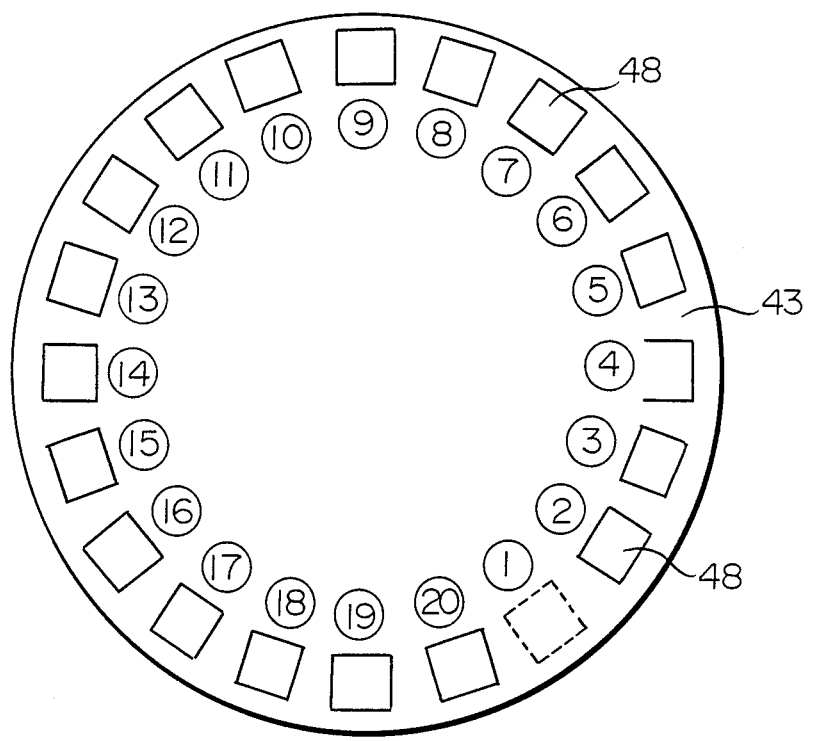
FIG. 8 is a top plan view of the disk.

Along the circumferential edge of the disk 43, there are disposed slide receivers 48 therein, each at an equal angle relative to an adjacent one, as shown in FIG. 8, being open at the circumference, wherein an opening 48a formed on the upper face of each receiver 48 is closed with an air-tight sealing lid 49 that serves as a closure means and fits into position. The sealing lid 49 is designed to resiliently press the inserted slide 2 from above. Radially from the circumference of the disk 43 there are formed grooves 43a therein, one between two adjacent slide receivers 48, and there is provided a revolving plate 50 with its axis coinciding with the circumference of the disk 43 and holding a pin 51 eccentrically positioned at the bottom which fits into and comes out of the grooves 43a as the revolving plate 50 is rotated in the direction of the arrow by a driving motor 52 placed thereabove. This driving motor 52 is actuated based on a signal from the driving circuit 37 so as to rotate the disk 43. There is also provided a disk-stopping device 53 which stops the disk 43 always at a correct position.

The embodiment described here has 20 such slide receivers 48, identified as address 1 through address 20 as shown in FIG. 8, of which address 1 is set as a part for calibration and the remaining 19 slide receivers, address 2 through address 20, are left open to 19 slides to be analyzed 2. Once a power switch provided on an appropriate position on the analyzer body 11 is turned ON, the disk 43 rotates in order to discharge possibly remaining slides which will be described later, and then stops with the slide receiver 48 of Address 2 at the position aligned with the slide insertion part 12 on the front of the analyzer body 11. Once a first slide to be analyzed 2 is inserted into the slide receiver 48 of Address 2, the insertion is detected by a slide insertion sensor 55 mounted on a sensor mount 54, and an insertion complete signal relevant thereto is loaded into the CPU 39 through the interface 38, and the CPU 39, upon receiving this signal, actuates the driving motor 52 through the driving circuit 37, moving the disk 43 forward one receiver position, so that a slide receiver 48 of Address 3 is aligned with the slide insertion part 12 to allow a second slide 2 to be inserted. Having been moved forward one receiver position, the first slide to be analyzed 2 positioned at Address 2 is now temporarily placed facing a disk address reading sensor 56 and a measurement item ID code-reading sensor 57, thereby the address on the disk 43 as well as the measurement item ID code are read by the sensors. The above-mentioned operation is repeated in sequence for a set number of slides to be analyzed, and the CPU 39 processes the data readout transferred via the interface 38, storing the addresses on the disk and the measurement items in a RAM 59 and selecting a measurement mode out of 0, 1, 2 and 3, which will be described later. A ROM 58 has a pre-written program that controls the CPU 39. Based on this program, the CPU 39 reads external data as required via the interface, or communicates data with the RAM, in order to perform arithmetic operations, and the CPU 39 loads data, generated as required, into the interface 38.

The specimen dripping part 13 mentioned previously has a specimen dripping hole 60 positioned outside of the disk 43. This specimen dripping hole 60 is closed by a shutter 62 under the force of a spring 61 when not in use. Slide reciprocating means 63 is provided inside the disk 43 in order to align the analyzing element 29 of the slide to be analyzed 2 with the specimen dripping hole 60. This slide reciprocating means 63 has a slide-pushing plate 64, which is slidably movable radially, and is connected via a link 65 with a plunger 66a of a dripping solenoid 66. The link 65 is pivotally movable on an axle 67. The dripping solenoid 66 is controlled by the CPU 39, and once it is energized, the plunger 66a is drawn against the force of the spring 68, causing the slide-pushing plate 64 to move in the arrow direction "a", thereby the slide 2 is pushed outward. Accordingly, the shutter 62 is pushed back against the force of the spring 61, thereby the dripping hole 60 is exposed, and the analyzing element 29 of the slide 2 is brought exactly under the specimen dripping hole 60 hole, completing a state where the specimen can be dripped.

The slide reciprocating means 63 is driven in a manner as follows: for first specimen dripping, once the "dripping start" key 26 on the "operation/control section" 17 on the analyzer body 11 is pressed, the CPU 39 energizes the dripping solenoid 66, causing a slide 2 to be pushed outside the slide receiver 48. For next specimen dripping onwards, the slide reciprocating means 63 operates automatically. After completion of specimen dripping, once the the "dripping complete" key 27 is pressed, the dripping solenoid 66 is turned off, and the slide-pushing plate 64, drawn by the spring 68, is retracted in the direction of the arrow "b", thus the slide 2 undergone specimen dripping returns to the corresponding slide receiver 48.

At the slide discharge port 14, there is provided a slide-discharging means 69 that discharges, outside the analyzer, the slides 2 having undergone photometric measurement. The slide-pushing plate 70 of this slide-discharging means pushes out the slides 2 as it moves in the direction of the arrow "a". The slide-pushing plate 70 is connected to the plunger 72a of a discharging solenoid 72 via a link 71 which is pivotally movable on the axle 73 and, when at rest, is pressed toward the inside of the disk 43, as drawn by a spring 74. When the discharging solenoid 72 is turned on to draw the plunger 72a in counter action against the force of the spring 74 so that the analyzed slide 2 in a slide receiver 48 is discharged from the analyzer. Once the discharging solenoid 72 is turned off, the slide-pushing plate 70 is retracted in the direction of the arrow "b". This retraction of the slide-pushing plate 70 is detected by a slide discharge sensor 5. The above-mentioned slide-discharging operation is repeated until all the analyzed slides 2 are discharged, and then the slide discharge sensor 75 outputs a signal signifying the completion of the discharge.

Figure 9:
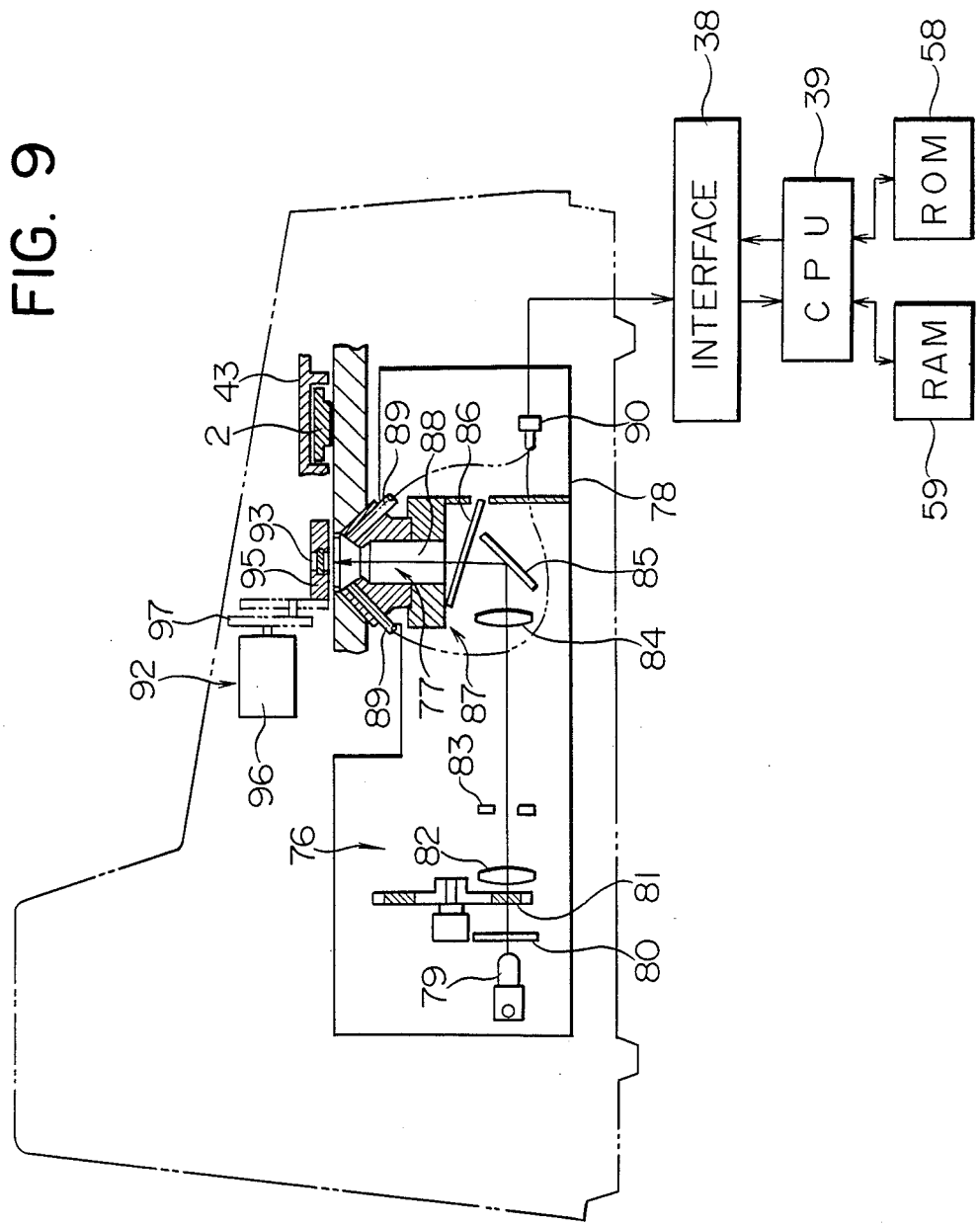
FIG. 9 illustrates the optical system in a cutaway view as well as block diagram.

FIG. 9 illustrates an optical system embodying the present invention. This optical system comprises an irradiation unit 76 and a photometric part 77, and is designed to optically measure the reaction, as to the status or result, of a liquid specimen dripped on a slide 2 with a reagent which is contained in the analysis element 29 in the slide 2, particularly by examining the change in density of the color caused by the reaction. The system is arranged in a sealed box 78, protected from dust and other extraneous matter. In the irradiation unit 76, the light rays generated by a tungsten lamp, halogen lamp, or the like at the light source 79 are made into a light beam of a specified wavelength relevant to the slide to be analyzed 2 (wavelength relevant to the measurement item) by transmission through a cold filter 80, interference filter 81, lens 82, diaphragm 83 and lens 84, deflected on a mirror 85, and, after being transmitted through a transparent glass plate 86, the beam is projected on the measurement surface of the slide 2 through an irradiation part 88 formed in a converging unit 87. The reflected light is, via an optical fiber 89 of the photometric part 77, directed to a photoelectric element 90, where converted into an electrical signal, thereby the reflection density, i.e. optical density is determined. Then, referring to the calibration curve generated by the CPU 39 based on a conversion formula for each measurement item, the CPU 39 determines an analysis value based on the resultant measurement value, and then, a printer 16 prints the analysis value onto a roll of recording sheet, and the print-out leaves an exit formed on the upper face of the analyzer body 11. As shown in FIG. 6, above the photometric part 77 is disposed a presser mechanism 91b that is energized by a presser solenoid 91a. The presser mechanism 91b in the course of a photometric operation presses a slide to be analyzed downward for stabilization, in order to ensure accurate measuring.

Numeral 92 represents a calibration mechanism. This is calibration means that calibrates the photometric system at earliest possible timing before a slide is subjected to photometric operation, and this calibration is necessary because the intensity of a lamp in the light source 79 may not be always constant due to aging, electrical noise, or the like. The calibration mechanism 92 is a unit that is capable of accurately measuring an optical density, and has a slide 95 comprising a first reference plate 93 of a pre-measured low density level and a second reference plate 94 of a higher optical density, wherein the slide 95 is linearly reciprocated by a motor 96.

The calibration mechanism 92 verifies the light intensity of the light source 79. More specifically, the slide 95 is reciprocated both before and after insertion (before specimen-dripping) of a slide 2, wherein the light from the light source 79 reflected by, for example, the second reference plate 94 of a higher optical density, and the reflected light is transmitted via the optical fiber 89 to the photoelectric element 90, where converted into an electrical signal. The CPU 39 determines light intensity based on the optical density, and verifies the light intensity of the light source 79.

Based on a predetermined reference light intensity for verification, the CPU 39 estimates the remaining service life of the light source 79 and checks insufficiency in light intensity. A warning may appear on the display 15 as to the remaining service life of the light source 79. At this state, however, the analyzer is still operatable. In the case of insufficiency of light intensity of the light source 79, an error message appears on the display 15, and the operation of the analyzer is inhibited.

Figure 10:
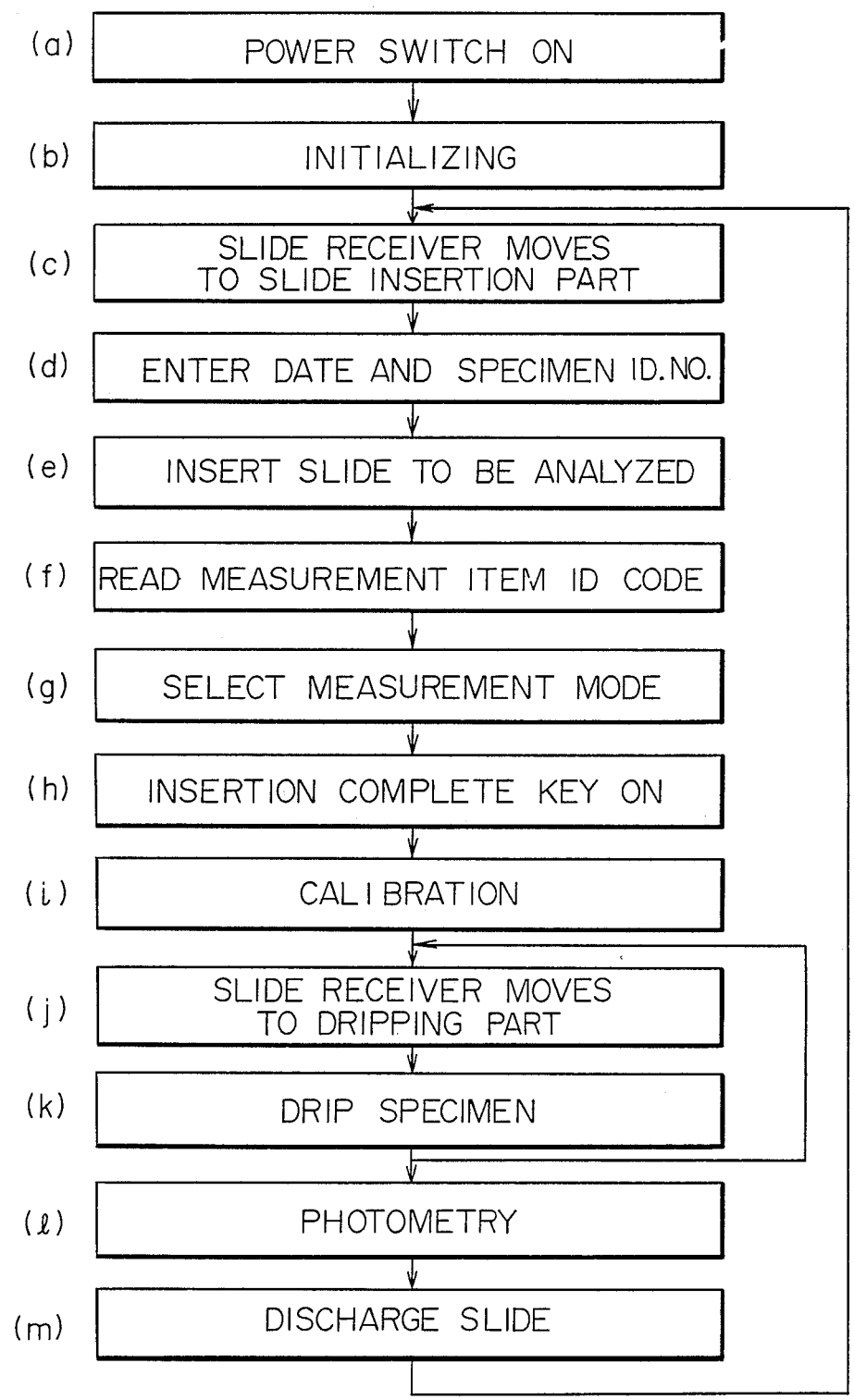
FIG. 10 is a flowchart explaining the operation sequence of this analyzer.

The operation sequence according to the present preferred embodiment of the invention is hereunder described referring to FIG. 10.

Once the power switch is turned on (Step a), the analyzer is initialized, where whether the calibration mechanism 92 is in an operatable position is detected and/or if there is a slide 2 not completely inserted into the slide insertion part 12, the slide 2 is pushed into position by the slide insertion roller 35 (Step b). Additionally, once the power switch is turned on, the incubation unit 36 is adjusted to a reaction temperature, and then, the measurement item ID code-reading sensor 57 detects whether there is a slide 2 in the disk 43, and, if there is a slide 2 remaining there, a slide receiver of an address of the remaining slide 2 is shifted to the position of the slide discharge part 14, and the slide is dischraged. Once that no slide receiver 48 has a slide 2 is detected, a slide receiver 48 of Address 2 is shifted to a position aligned with the slide insertion part 12 (Step c), and then, according to a specific requirement, an operator enters the current date, and specimen ID, by using numerical keys 18 on the operation/control section 17 (Step d).

Once the above-mentioned entry is complete, the slides to be analyzed 2 are loaded into position via the slide insertion part 12 (Step e). Once a first slide 2 is loaded into a slide receiver 48 of Address 2, the loading is detected by the slide insertion detection sensor 55, and the disk 43 is rotated one receiver position, and accordingly, a slide receiver of Address 3 is moved to the slide insertion part 12 on the analyzer body 11.

When a slide receiver 48 of Address 3 is aligned with the slide insertion part 12 on the analyzer body 11, the already inserted slide 2 of Address 2 rests in the halt position next to the slide insertion part 12, and at this position, an measurement item is read out using a code 32 (Step f), thereby the CPU selects a relevant measurement mode (Step g). Based on the so-read measurement item, the RAM 59 stores the data on which address's slide receiver 48 has a slide 2 of what measurement item, for example, GPT (rate measurement technique) or BUN (end point measurement technique).

Once all the slides to be subjected to photometric operation are loaded, the operator presses the insertion complete key 26 (Step h). Several seconds after, the slide insertion roller 35 stops, and Address 1 having not received a slide 2 and being vacant is moved to the photometric part 77. Then the calibration mechanism 92 disposed in the photometric part 77 is actuated to perform calibration (Step i). Next, the slide in the slide receiver 48 of Address 2 is shifted to the specimen dripping part 13 (Step j). Arrival of the slide 2 to the dripping part 13 is indicated by a buzzer or the like. Additionally, a specimen ID No., measurement item and the like appear on the display 15. Once verifying the indications on the display, the operator fills a pippet with a specimen being analyzed, and press the drip start key 26 on the operation/control section 17.

Pressing the drip start key 26 actuates the slide reciprocating means 63 so as to position the analysis element of the slide 2 exactly below the specimen dripping hole 60, and, at the same time, this positioning action allows the slide 2 press the shutter 62 to expose the specimen dripping hole 60. Next, the specimen in the pippet is dripped onto the analysis element 29 of the slide to through the specimen dripping hole 60 (Step k). Meanwhile, a duration from when the slide 2 is positioned exactly below the specimen dripping hole 60 to when the specimen is actually dripped is regulated by the CPU 39, in order to prevent from the shutter being open for an excessively long period.

Once specimen dripping is complete as mentioned above, the operator presses the dripping complete key 27. Then the slide reciprocating means 63 returns to its original position, and returns the slide 2 having received the specimen to the corresponding slide receiver 48 on the disk 43. Accordingly, the disk 43 rotates one receiver position, shifting a next address's slide 2 to the specimen dripping part 13. Once the dripping complete key 27 is pressed, the CPU 39 controls the duration from completion of dripping to photometric operation, for each slide to be analyzed; duration from dripping for a first slide to a photometric operation thereof (incubation duration); and a duration to second dripping.

Once all sides 2 have undergone specimen dripping, and when a predetermined time has elapsed, rotation of the disk 43 sequentially move the slide 2 of Address 2 onwards to the photometric part 77. The photometric part 77 performs a photometric operation (Step 1), and the printer 16 prints the analysis value onto a roll of recording sheet, that is discharged from the exit.

Once photometric operations with all the loaded slides 2 (slides undergone specimen dripping) are complete, these slides are sequentially transported to the slide discharge part 14, and are sequentially discharged outside (Step m). Once the discharging operation is complete, Address 2 is shifted to the slide insertion part 12, thus one cycle of analyzing operation is complete.

Figure 11:
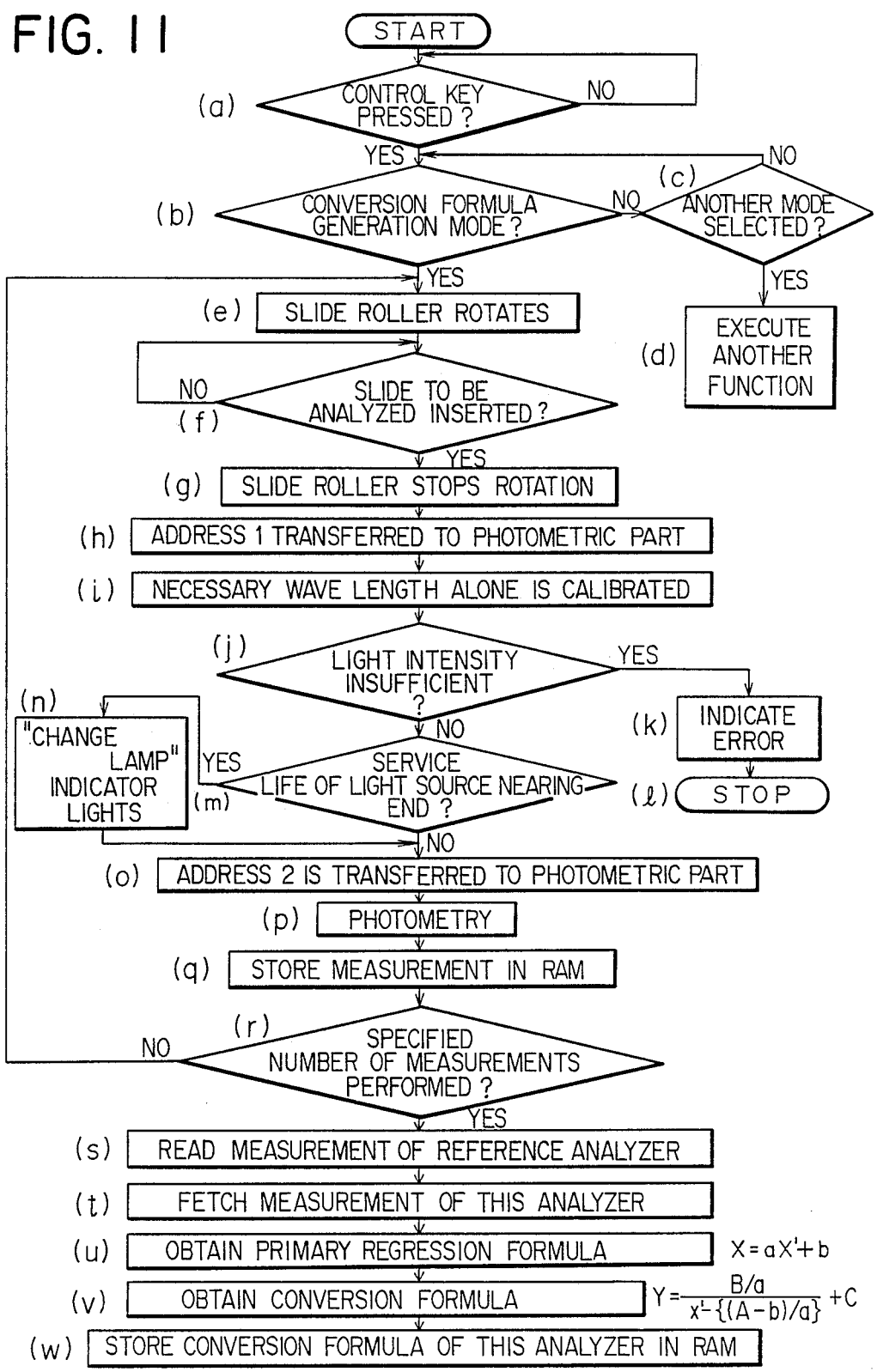
FIG. 11 is a flowchart explaining how a conversion formula is obtained.

The slides to be analyzed 2 are subjected to a measurement operation in such a manner. Meanwhile, to generate a conversion formula for obtaining an analysis value based on a measurement value obtained by the analyzer, the control key 25 is pressed, as in Steps a and b of FIG. 10, following initializing, and after Address 2 of the disk 43 is transferred to the slide insertion part 12. A flow chart for generating a conversion formula of another analyzer 4 is given in FIG. 11.

The reference analyzer 3 has, for example, the previously mentioned conversion formula (1).

Once the control key 25 on the analyzer 4 is operated, in Step a, which input of the control key 25 is judged; and in Step b, whether the conversion formula generation mode has been selected is judged. If the current mode is not the generation mode, in Step c whether another mode for example the cleaning mode has been selected is judged. If another mode has been selected, processing based on this mode is performed in Step d.

Once the conversion formula generation mode is selected, the slide insertion roller 35 is rotated (Step e) so as to insert predetermined numbers of the reference slides 1 into the currently vacant Addresses on and after 2 (Step f). Once the predetermined numbers of reference slides 1 are inserted, the slide insertion roller 35 stops rotating (Step g). Next, Address 1 is transferred to the photometric part 77 (Step h), and then, the calibration mechanism 92 disposed on the photometric part 77 is actuated, and the interference filter 81 whose characteristic wave length being one appropriate for measurement is fit into position thereby calibration is performed (Step i).

Next, whether light intensity is insufficient is judged (Step j). If the light intensity is insufficient, an error message appears on the display 15 (Step k), stopping the analyzer (Step 1). If the light intensity is sufficient, whether the service life of the light source 79 is terminating is judged (Step m). If the service life of the light source 79 is nearing its end, "CHANGE LAMP" message appears (Step n).

The reference slide 1 loaded into the slide receiver 48 in Address 2 is transferred to the photometric part (Step o), and subjected to a photometric operation (Step p). The obtained measurement value on optical reflection density is stored in the RAM 59 (Step q). Thereafter, next reference slides 1 being loaded in addresses on and after 3 are sequentially transferred to the photometric part, thereby predetermined numbers of measurements are obtained (Step r).

A measurement operation, using the reference slides 1, in such a manner is also performed with the reference analyzer 3. The measurement values obtained by the reference analyzer 3 are read by a personal computer connected to the analyzer 3 (Step s). Based on this measurement values as well as based on a measurement values read from the RAM 59 of the analyzer 4 (Step t), the primary regression formula relevant to these measurement values is generated (Step u). Then the primary regression formula is substituted into the term in the conversion formula on the reference analyzer 3, thereby the conversion formula (3) relevant to the another analyzer 4 is generated (Step v), and the so-obtained conversion formula (3) is loaded into the RAM 59 (Step w), thereby an analytical curve is generated.

From then onwards, an analysis value of the analyzer 4 is determined by referring to the analytical curve generated using the conversion formula (3) based on a measurement value of a slide to be analyzed 2, wherein the analysis value is same as a measurement value of the reference analyzer 3. In this way, generating a conversion formula is performed using a reference slide 1. Accordingly, in contrast with a conversion formula generating technique based on specimen dripping onto a slide to be analyzed 2, this technique of the invention can reduce fluctuation in measurement values, and can decrease operation cost since the reference slide 1 is reusable, and, in addition, this technique eliminates an incubation duration, thereby an analyzer is readily matched with the reference analyzer 3.

Figure 12:
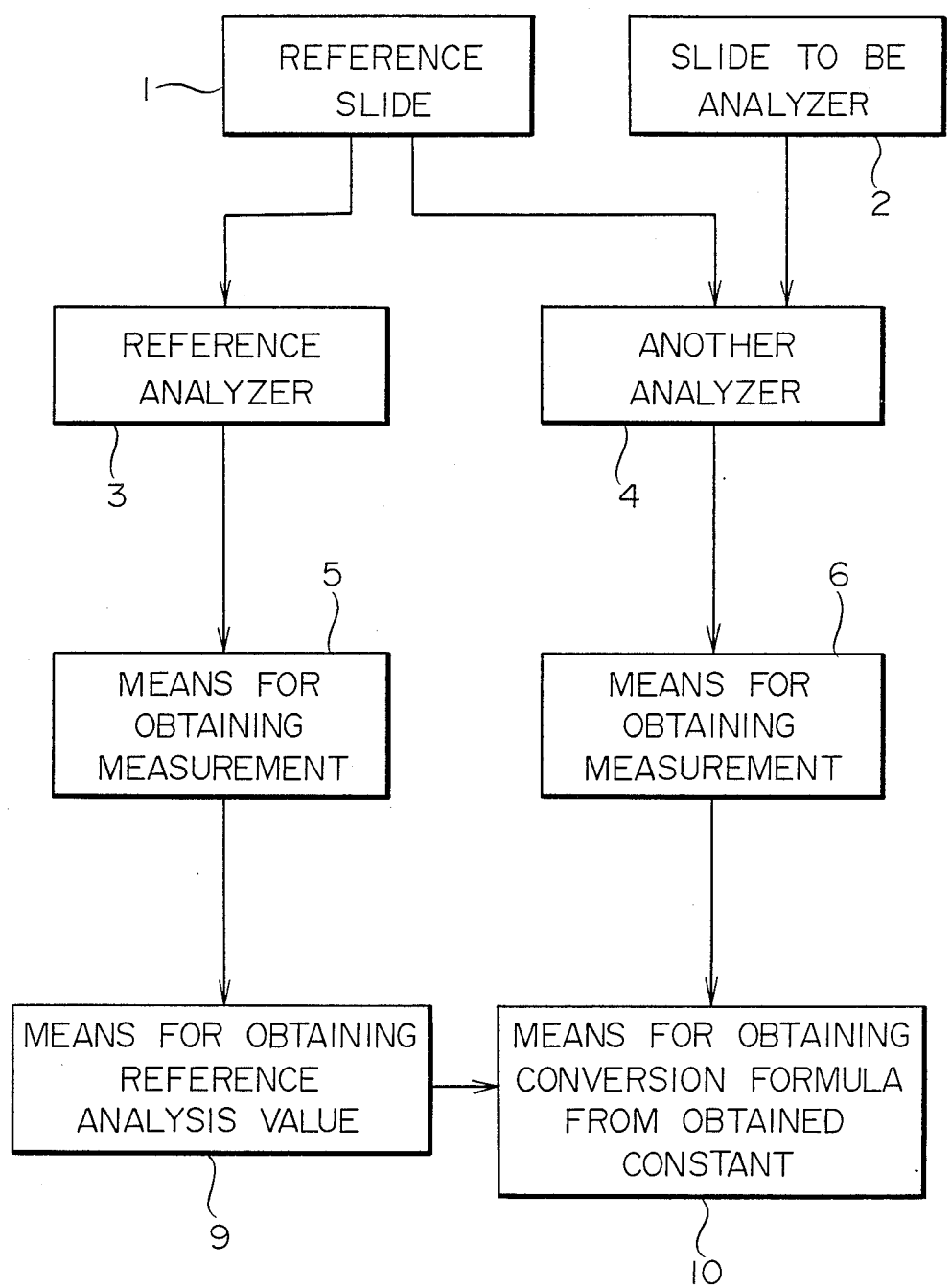
FIG. 12 is a block diagram explaining another preferred embodiment of the invention.

FIG. 12 shows another preferred embodiment of the invention.

In this embodiment, using a reference analyzer 3 and another analyzer 4, a reference slide 1 is subjected to measurement specific times corresponding with a number of constants in a conversion formula that obtains an analysis value based on a measurement value.

For example, when generating a conversion formula (1) mentioned previously, three reference slides 1 are subjected to measuring, and independent means for obtaining measurement values 5 and 6 determine measurement values, correspondingly, $X_{11}$, $X_{12}$, and $X_{13}$; and $X_{21}$, $X_{22}$, and $X_{23}$. Otherwise, using one such means, and using a plurality of reference slides, the obtained measurement values may be averaged.

Next, using means 9 for obtaining reference analysis value, reference analysis values $Y_{11}$ through $Y_{13}$ are determined based on the measurement values $X_{12}$ through $X_{13}$ that have been obtained by the reference analyzer 3, wherein conversion formulas used are:

$$Y_{11} = \frac{B_1}{X_{11} - A_1} + C_1$$

$$Y_{12} = \frac{B_1}{X_{12} - A_1} + C_1$$

$$Y_{13} = \frac{B_1}{X_{13} - A_1} + C_1$$

wherein constants $A_1$, $B_1$, and $C_1$ in the formulas are predetermined ones.

Using means for obtaining conversion formula 10, constants are obtained based on the so-obtained reference analysis values as well as based on the measurement values obtained by the analyzer 4.

For example, based on reference analysis values $Y_{11}$ through $Y_{13}$ as well as based on the measurement values $X_{21}$ through $X_{23}$, constants $A_2$, $B_2$, and $C_2$ are determined using the conversion formulas below:

$$Y_{11} = \frac{B_2}{X_{21} - A_2} + C_2$$

$$Y_{12} = \frac{B_2}{X_{22} - A_2} + C_2$$

$$Y_{13} = \frac{B_2}{X_{23} - A_2} + C_2$$

wherein the conversion formulas into which these constants have been substituted are written onto a RAM 59 on the analyzer 4. Instead of being written onto the RAM 59, these conversion formulas may be stored in a ROM 58.

As can be understood from the description above, according to the method of the invention for generating a conversion formula that is used for obtaining analysis values, a plurality of reference slides are subjected to measuring operations with a reference analyzer as well as another analyzer, wherein based on each of the so-obtained measurement values, the analysis values of another analyzer are adjusted to those of the reference analyzer. Therefore, actually dripping a specimen onto a slide to be analyzed is not necessary, thereby measurement value fluctuation possibly caused by actual specimen dripping is eliminated. Additionally, use of a reference slide eliminates specimen dripping and reaction time, thereby the conversion formula is readily incorporated into an analyzer other than the reference analyzer, at a lower cost, in a shorter period.

What is claimed is:

1. A method of producing an analytical curve for an analyzing apparatus, the apparatus providing an analysis result on the basis of said analytical curve in response to a measurement value obtained by photoelectrically measuring light intensity reflected from a slide to be analyzed, the method comprising the steps of:

measuring a plurality of reference slides by using a first analyzing apparatus which has a predetermined analytical curve, thereby obtaining a plurality of first measurement values and providing a plurality of first analysis results;

measuring said plurality of reference slides by using a second analyzing apparatus, thereby obtaining a plurality of second measurement values; and producing an analytical curve for said second analyzing apparatus to provide a plurality of second analysis results on the basis of a relation between said first measurement values and said second measurement values so that said plurality of second analysis results correspond to said plurality of first analysis results.

2. The method of claim 1, wherein said reference slide is made of color paper, plastic or ceramic.

3. The method of claim 1, wherein said reference slide is dyed in a predetermined color so as to provide a predetermined reflection density.

4. The method of claim 1, wherein said measuring step includes the step of storing said measurement values in a memory.

5. The method of claim 1, wherein said predetermined analytical curve is represented by a conversion formula having a variable measurement value, and wherein the step of producing an analytical curve comprises the substeps of processing said first measurement values and said second measurement values so as to provide a regression formula, substituting said variable measurement value with said regression formula to provide a revised conversion formula, and storing the revised conversion formula as said analytical curve for said second analyzing apparatus in a memory of said second analyzing apparatus.

6. A method of claim 1, wherein said relation between said first measurement values and said second measurement values is represented by a regression formula and said predetermined analytical curve is represented by a conversion formula, and wherein said analytical curve for said second analyzing apparatus is represented by a formula obtained by combining said regression formula and said conversion formula.

7. The method of claim 5, wherein said conversion formula is represented by $Y = B/(X-A) + C,$ in which Y is an analysis result, X is a measurement value, and A, B and C are constants.

8. The method of claim 6, wherein said regression formula is a primary regression formula represented by $X = aX' + b$ in which X is a measurement value obtained by the first analyzing apparatus, X' is a measurement value obtained by the second analyzing apparatus, and a and b are constant.

9. The method of claim 1,
wherein said first and second analyzing apparatus provide an analysis result for analysis items using End-Point Assay and Rate Assay.

10. The method of claim 9,
wherein said analysis items in accordance with End-Point Assay are glucose, total cholesterol, hemoglobin, urea nitrogen, urea acid, total protein, albumin, triglyceride, and total bilirubin.

11. The method of claim 9, wherein said analysis items analyzed using Rate Assay are glutamic-oxaloacetic transaminase, glutamin-pyruvic transaminase, alkaline phosphatase, and lactate dehydrogenase.

12. The method of claim 1, wherein said step of measuring a plurality of reference slides by both said first and second analyzing apparatus comprises substeps of
loading said plurality of reference slides onto said analyzing apparatus,
checking the condition of light source by a calibration mechanism, and
performing a photometric operation for said loaded reference slides with said checked light source.

13. The method of claim 12,
wherein said step of checking the calibration of light source includes the steps of calibrating wavelength, judging the sufficiency of light intensity, and judging whether the end of the service life has been reached.

* * * * *